(12) United States Patent
Jackson et al.

(10) Patent No.: US 10,548,641 B2
(45) Date of Patent: Feb. 4, 2020

(54) MEDICAL IMPLANT RECEIVERS HAVING DUAL LEAD IN CLOSURE MATING THREAD FORMS

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 15/964,502

(22) Filed: Apr. 27, 2018

(65) Prior Publication Data

US 2018/0243013 A1 Aug. 30, 2018

Related U.S. Application Data

(63) Continuation of application No. 15/469,076, filed on Mar. 24, 2017, now Pat. No. 9,956,004, which is a continuation of application No. 14/566,356, filed on Dec. 10, 2014, now Pat. No. 9,636,146, which is a continuation of application No. 13/694,849, filed on Jan. 10, 2013, now Pat. No. 8,911,479.

(60) Provisional application No. 61/631,746, filed on Jan. 10, 2012, provisional application No. 61/634,361, filed on Feb. 28, 2012.

(51) Int. Cl.
*A61B 17/70* (2006.01)
*A61B 17/86* (2006.01)

(52) U.S. Cl.
CPC ...... *A61B 17/7035* (2013.01); *A61B 17/7032* (2013.01); *A61B 17/863* (2013.01); *A61B 17/8665* (2013.01); *A61B 17/8685* (2013.01); *A61B 2017/8655* (2013.01)

(58) Field of Classification Search
CPC ............ A61B 17/7035; A61B 17/7032; A61B 17/863; A61B 17/8665; A61B 17/8685; A61B 2017/8655
USPC ....... 606/246, 264–273, 275, 278, 279, 305, 606/308, 315, 316; 403/362; 411/393
See application file for complete search history.

(56) References Cited

U.S. PATENT DOCUMENTS 2,005,348 A 6/1935 Michell
2,244,046 A 6/1941 Bradshaw
(Continued)

FOREIGN PATENT DOCUMENTS

DE 20207850 U1 10/2002
EP 1316294 A2 6/2003
(Continued)

OTHER PUBLICATIONS

U.S. Appl. No. 16/391,049, filed Apr. 22, 2019, Jackson et al.

*Primary Examiner* — Pedro Philogene
*Assistant Examiner* — David C Comstock
(74) *Attorney, Agent, or Firm* — Polsinelli PC

(57) ABSTRACT

An open implant closure structure includes a helically wound guide and advancement structure having at least two helically wound forms thereon providing a multi-start closing mechanism for use between spaced arms of a cooperating open medical implant having mating helically wound structure thereon. Illustrated structures include interlocking flange forms, v-threads, square threads, reverse angle threads and buttress threads and receivers with break-off extensions and cooperating tooling.

28 Claims, 7 Drawing Sheets

(56) References Cited

U.S. PATENT DOCUMENTS

| | | | |
|---|---|---|---|
| 2,833,325 A | 5/1958 | Laisy | |
| 3,963,322 A | 6/1976 | Gryctko | |
| 4,528,874 A | 7/1985 | Dunn | |
| 4,600,225 A | 7/1986 | Blose | |
| 5,067,955 A | 11/1991 | Cotrel | |
| 5,092,635 A | 3/1992 | DeLange et al. | |
| 5,171,279 A | 12/1992 | Mathews | |
| 5,217,497 A | 6/1993 | Mehdian | |
| 5,234,430 A | 8/1993 | Huebner | |
| 5,334,203 A | 8/1994 | Wagner | |
| 5,605,458 A | 2/1997 | Bailey et al. | |
| 5,607,304 A | 3/1997 | Bailey et al. | |
| 5,672,176 A | 9/1997 | Biedermann et al. | |
| 5,797,911 A | 8/1998 | Sherman et al. | |
| 5,961,517 A | 10/1999 | Biedermann et al. | |
| 6,006,930 A | 12/1999 | Dreyer et al. | |
| 6,010,502 A * | 1/2000 | Bagby | A61F 2/44 606/247 |
| 6,063,090 A | 5/2000 | Schlapfer | |
| 6,077,262 A | 6/2000 | Schlapfer et al. | |
| 6,077,267 A | 6/2000 | Huene | |
| 6,254,146 B1 | 7/2001 | Church | |
| 6,296,642 B1 | 10/2001 | Morrison et al. | |
| 6,412,831 B1 | 7/2002 | Noel et al. | |
| 6,443,953 B1 | 9/2002 | Perra et al. | |
| 6,485,491 B1 | 11/2002 | Farris et al. | |
| 6,520,962 B1 | 2/2003 | Taylor et al. | |
| 6,554,834 B1 | 4/2003 | Crozet et al. | |
| 6,730,089 B2 | 5/2004 | Jackson | |
| 6,835,196 B2 | 12/2004 | Biedermann et al. | |
| 6,997,927 B2 | 2/2006 | Jackson | |
| 7,204,838 B2 | 4/2007 | Jackson | |
| 7,250,052 B2 | 7/2007 | Landry et al. | |
| 7,591,839 B2 | 9/2009 | Biedermann et al. | |
| 7,717,942 B2 | 5/2010 | Schumacher | |
| 7,766,945 B2 | 8/2010 | Nilsson et al. | |
| 7,794,477 B2 | 9/2010 | Melkent et al. | |
| 7,857,834 B2 | 12/2010 | Boschert | |
| 7,972,364 B2 | 7/2011 | Biedermann et al. | |
| 8,092,494 B2 | 1/2012 | Butler et al. | |
| 8,162,989 B2 | 4/2012 | Khalili | |
| 8,382,809 B2 | 2/2013 | Kaufman et al. | |
| 8,814,913 B2 | 8/2014 | Jackson | |
| 8,828,060 B2 | 9/2014 | Biedermann et al. | |
| 8,911,479 B2 | 12/2014 | Jackson et al. | |
| 8,998,956 B2 * | 4/2015 | George | A61B 17/0642 606/250 |
| 9,068,587 B2 | 6/2015 | Sage et al. | |
| 9,445,847 B2 | 9/2016 | Biedermann et al. | |
| 9,636,146 B2 | 5/2017 | Jackson et al. | |
| 9,717,533 B2 | 8/2017 | Jackson et al. | |
| 9,743,957 B2 | 8/2017 | Jackson | |
| 9,861,394 B2 | 1/2018 | Jackson | |
| 10,004,541 B1 | 6/2018 | Jackson | |
| 2002/0120272 A1 * | 8/2002 | Yuan | A61B 17/7032 606/276 |
| 2002/0143341 A1 | 10/2002 | Biedermann et al. | |
| 2003/0023243 A1 | 1/2003 | Biedermann et al. | |
| 2003/0100904 A1 | 5/2003 | Biedermann | |
| 2003/0149431 A1 | 8/2003 | Varieur et al. | |
| 2003/0199873 A1 * | 10/2003 | Richelsoph | A61B 17/7032 606/278 |
| 2004/0039383 A1 | 2/2004 | Jackson | |
| 2004/0049196 A1 | 3/2004 | Jackson | |
| 2004/0138662 A1 | 7/2004 | Landry et al. | |
| 2004/0143265 A1 | 7/2004 | Landry | |
| 2004/0147929 A1 | 7/2004 | Biedermann et al. | |
| 2004/0167524 A1 | 8/2004 | Jackson | |
| 2004/0167525 A1 | 8/2004 | Jackson | |
| 2004/0172032 A1 | 9/2004 | Jackson | |
| 2004/0186474 A1 | 9/2004 | Matthis et al. | |
| 2005/0131421 A1 * | 6/2005 | Anderson | A61B 17/00234 606/99 |
| 2005/0182410 A1 * | 8/2005 | Jackson | A61B 17/7032 606/278 |
| 2005/0216003 A1 | 9/2005 | Biedermann et al. | |
| 2005/0277928 A1 | 12/2005 | Boschert | |
| 2006/0009773 A1 | 1/2006 | Jackson | |
| 2006/0083603 A1 | 4/2006 | Jackson | |
| 2007/0208344 A1 | 9/2007 | Young | |
| 2008/0215100 A1 | 9/2008 | Matthis et al. | |
| 2008/0269809 A1 | 10/2008 | Garamszegi | |
| 2008/0292429 A1 | 11/2008 | Hasenbohler et al. | |
| 2011/0152947 A1 | 6/2011 | Kirschman | |
| 2011/0270321 A1 | 11/2011 | Prevost et al. | |
| 2013/0013003 A1 | 1/2013 | Carbone et al. | |
| 2014/0081334 A1 | 3/2014 | Jackson | |
| 2014/0142633 A1 | 5/2014 | Jackson et al. | |
| 2014/0214097 A1 | 7/2014 | Jackson et al. | |
| 2015/0119942 A1 | 4/2015 | Jackson et al. | |
| 2015/0148846 A1 | 5/2015 | Jackson | |
| 2015/0164558 A1 | 6/2015 | Jackson et al. | |
| 2016/0038188 A1 | 2/2016 | Jackson et al. | |
| 2016/0242818 A1 | 8/2016 | Jackson | |
| 2017/0189073 A1 | 7/2017 | Jackson et al. | |
| 2017/0333083 A1 | 11/2017 | Jackson et al. | |
| 2017/0354441 A1 | 12/2017 | Jackson et al. | |
| 2017/0354443 A1 | 12/2017 | Jackson | |
| 2018/0132901 A1 | 5/2018 | Jackson et al. | |
| 2018/0296249 A1 | 10/2018 | Jackson | |
| 2019/0231400 A1 | 8/2019 | Jackson et al. | |

FOREIGN PATENT DOCUMENTS

| | | |
|---|---|---|
| EP | 1570796 A1 | 9/2005 |
| WO | WO 95/13755 | 5/1995 |
| WO | WO 02/076314 | 10/2002 |

* cited by examiner

Fig. 15.
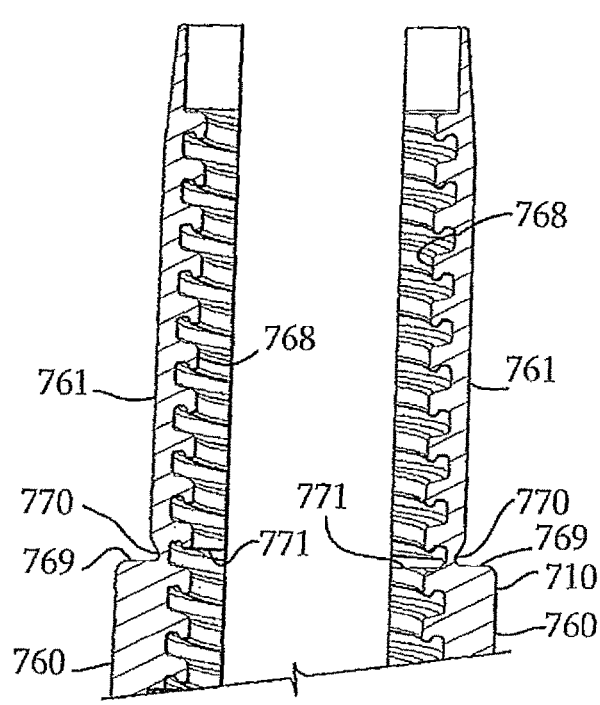
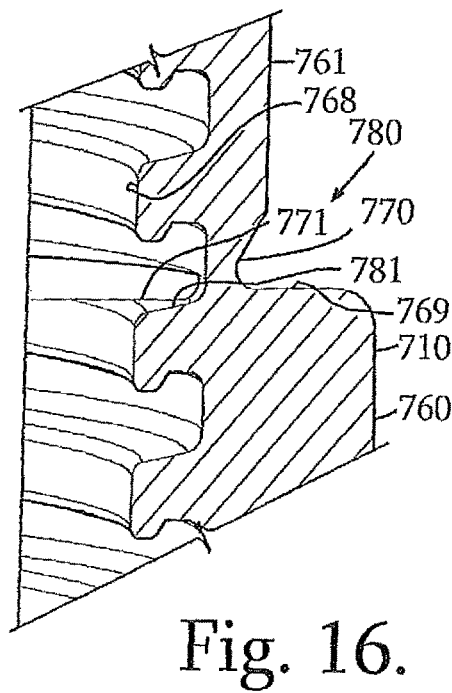
Fig. 16.
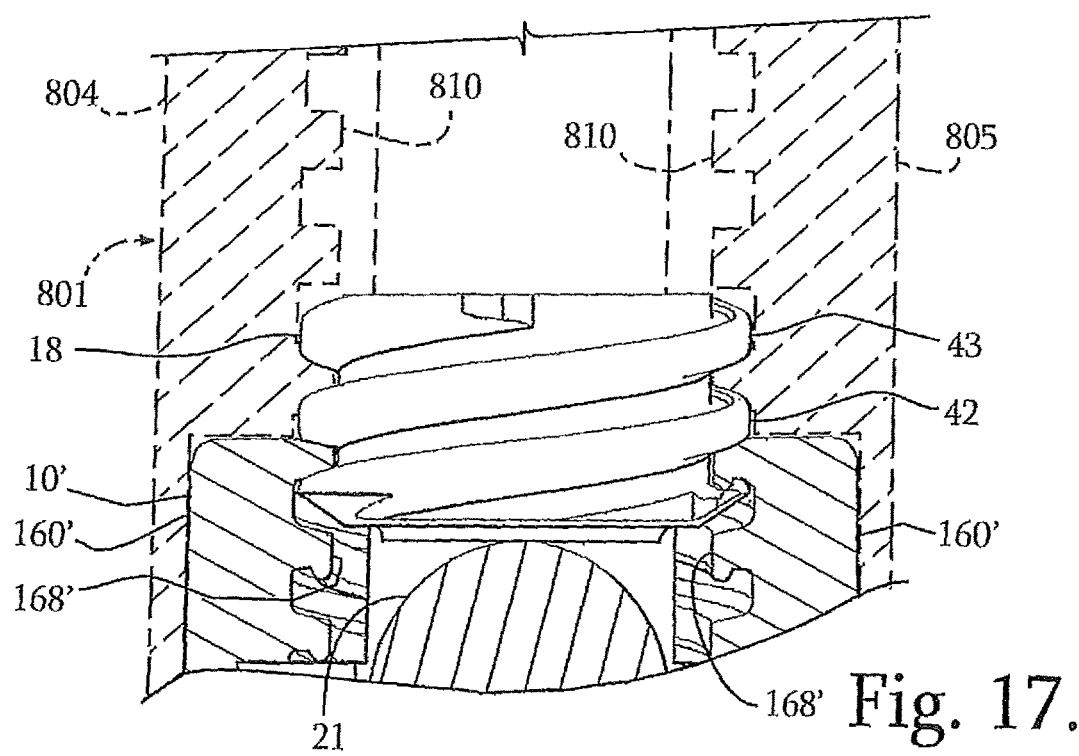
Fig. 17.

MEDICAL IMPLANT RECEIVERS HAVING DUAL LEAD IN CLOSURE MATING THREAD FORMS

CROSS-REFERENCE TO RELATED APPLICATIONS

The present application is a continuation of U.S. patent application Ser. No. 15/469,076, filed Mar. 24, 2017, which is a continuation of U.S. patent application Ser. No. 14/566, 356, filed Dec. 10, 2014, now U.S. Pat. No. 9,636,146, which is a continuation of U.S. patent application Ser. No. 13/694,849, filed Jan. 10, 2013, now U.S. Pat. No. 8,911, 479, issued Dec. 16, 2014, which claims the benefit of U.S. Provisional Application No. 61/631,746, filed Jan. 10, 2012 and U.S. Provisional Application No. 61/634,361, filed Feb. 28, 2012, all of which are incorporated by reference herein for all purposes.

BACKGROUND OF THE INVENTION

The present invention is directed to structure for joining together parts of a medical implant, in particular to closure mechanisms for use with open bone anchors in spinal surgery, and in some embodiments thereof, for use with spinal bone anchors such as polyaxial screws.

Bone anchors, such as bone screws and hooks are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a rod or are supported by the rod. Although both closed-ended and open-ended bone anchors are known, open-ended anchors are particularly well suited for connections to longitudinal connecting members such as hard, soft or deformable rods, dynamic or elastic connectors and connector arms, because such rods or other connector members do not need to be passed through a closed bore, but rather can be laid or urged into an open channel within a receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit.

Typical open-ended bone screws include a threaded shank with a head or receiver having a pair of parallel projecting branches or arms which form a yoke with a U-shaped slot or channel to receive a rod or other longitudinal connecting member. Hooks and other types of connectors, as are used in spinal fixation techniques, may also include similar open ends for receiving rods or portions of other fixation and stabilization structure. The open-ended head or rod receiver portion of such implants typically includes a pair of spaced arms forming a channel closed by a closure member after the rod or other longitudinal connecting member is placed in the channel. Known closures include slide-on types, twist-on varieties that are rotated ninety degrees to a locked in position, and a variety of single start helically wound guide and advancement structures including, for example, thread forms having v-thread, reverse-angle buttress or square thread forms, to name a few, as well as other non-threadlike helically wound forms. Sometimes threaded plugs are utilized with outer threaded nuts to prevent splaying of the receiver arms.

As indicated above, the force required to press a closure structure down onto a rod or other connector located between arms of an open implant is considerable. Even though a head or receiver portion of an open polyaxial bone anchor may be pivoted in a direction to make it easier for the arms of the open implant to receive a rod or other connector, spinal misalignments, irregularities and the placement of other surgical tools make it difficult to place the rod or other connector between the arms of the implant while a closure structure is mated with the open implant as well as used to push the rod or other connector downwardly into the implant. For example, when the closure is a cylindrical plug having a single start helically wound guide and advancement structure, such structure must be aligned with mating structure on one of the implant arms and then rotated until a portion of the structure is captured by mating guide and advancement structure on both arms of the implant, all the while the closure is being pressed down on the rod while other forces are pushing and pulling the rod back out of the implant. Integral or mono-axial open implants that cannot be pivoted to receive the rod are even more difficult to manipulate during the initial placement of the rod and initial mating rotation of a closure plug between the spaced, open arms of the implant. Therefore, extraordinary forces are placed on the implant and closure plug while the surgeon either pushes down on the rod or pulls up on the bone to get the rod in position between the implant arms and to initially push down upon the rod with the closure plug.

SUMMARY OF THE INVENTION

A closure structure, top or plug of the invention for insertion between spaced arms of an open medical implant includes one or more helically wound guide and advancement features, each feature having a start surface or structure located at or near a bottom surface of the closure plug, each start structure simultaneously engaging and being captured by each of the spaced arms of the open implant upon initial rotation of the closure structure with respect to the open implant arms. According to an aspect of the invention, a double-start closure is disclosed having two helically wound forms thereon, each form having a start structure for simultaneously engaging a mating helical form on a respective open implant arm. Each time the illustrated duel- or double-start closure plug is rotated one turn (three hundred sixty degrees) between the implant arms, the closure plug advances axially into the implant and toward the rod by a width of two helical forms. The helically wound forms of the multi-start closure spiral around a cylindrical plug body thereof to an extent that the closure rotates over ninety degrees to fully or substantially receive the entire closure plug between the arms of the open implant. The illustrated closure is sized for at least one complete rotation (three hundred sixty degrees) of the plug with respect to the open implant to substantially receive the plug between the implant arms. Multi-start closures of the invention may have two or more coarse or fine helical forms, resulting in fewer or greater forms per axial distance spiraling about the closure plug body and thus resulting in plugs that rotate less (when more coarse) or more (when thin or fine) than one complete rotation to be fully received between the implant arms, typically, at least a ninety-one degree rotation is preferred.

An illustrated multi-start closure and mating open implant is in the form of non-threaded, interlocking flange forms.

Also disclosed are multi-start closure structures provided with helically wound forms of other geometry, including, but not limited to helically wound threads such as reverse angle, buttress, square and v-threads. The multi-start closure may be cannulated for minimally invasive surgical applications.

Another illustrated multi-start closure embodiment of the invention is shown with a bone screw assembly having an open receiver with a pair of opposed arms, each arm having guide and advancement structure for simultaneous mating engagement with a start of the helically wound multi-start closure. A further embodiment according to the invention includes an open bone anchor receiver having integral upwardly extending break-off tabs that also have the guide and advancement structure for mating with the multi-start closure. A further embodiment includes an attachable/detachable guide tool cooperating with such a multi-start open receiver, the tool having inner guide and advancement structures located near a bottom thereof for rotatably and matingly receiving the multi-start closure and being synchronized with the receiver guide and advancement structure for rotating and driving the multi-start closure downward from the guide tool to the receiver.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 15 is a partial front elevational view of an embodiment of a multi-start open bone anchor receiver of an embodiment of the invention with portions broken away to show the detail thereof, the receiver including break-off tabs.

FIG. 16 is an enlarged and partial front elevational view of the receiver of FIG. 15 with portions broken away to show the detail thereof.

FIG. 17 is a partial front elevational view of an embodiment of a bone anchor receiver having a guide and advancement structure that matingly cooperates with the multi-start closure of FIG. 1, also shown in front elevation, the receiver having portions broken away to show the detail thereof, and further shown with a guide tool, shown in phantom, the guide tool having a multi-start guide and advancement structure receiving inner surface synchronized with the bone anchor receiver guide and advancement structure.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Furthermore, the terms lead, pitch and start, as such terms are used to describe helically wound guide and advancement structures, are to be understood as follows: Lead is a distance along the axis of a closure plug that is covered by one complete rotation (360 degrees) of the closure plug with respect to a mating open implant. Pitch is the distance from a crest (or outer point or location) of one guide and advancement structure form to the next. For example in a single-start thread-form, such as a single start, helically wound v-thread closure plug, lead and pitch are the same. Single start means that there is only one ridge or helically wound form wrapped around a cylindrical core, or in the case of the present invention, wrapped around a cylindrical closure plug body and thus there is only one start structure or surface at a base or forward end of the closure body that initially engages a mating structure on the open implant. Each time a single start closure rotates one turn (360 degrees), the closure has advanced axially by a width of one ridge or one helical form. Double-start means that there are two ridges or forms wrapped around a core body and thus there are two starting surfaces or structures on the closure plug. Therefore, each time a double-start body rotates one turn (360 degrees), such a body has advanced axially by a width of two ridges or forms. Multi-start means that there are at least two and may be up to three or more of such ridges or forms wrapped around a core body.

Figure 8:
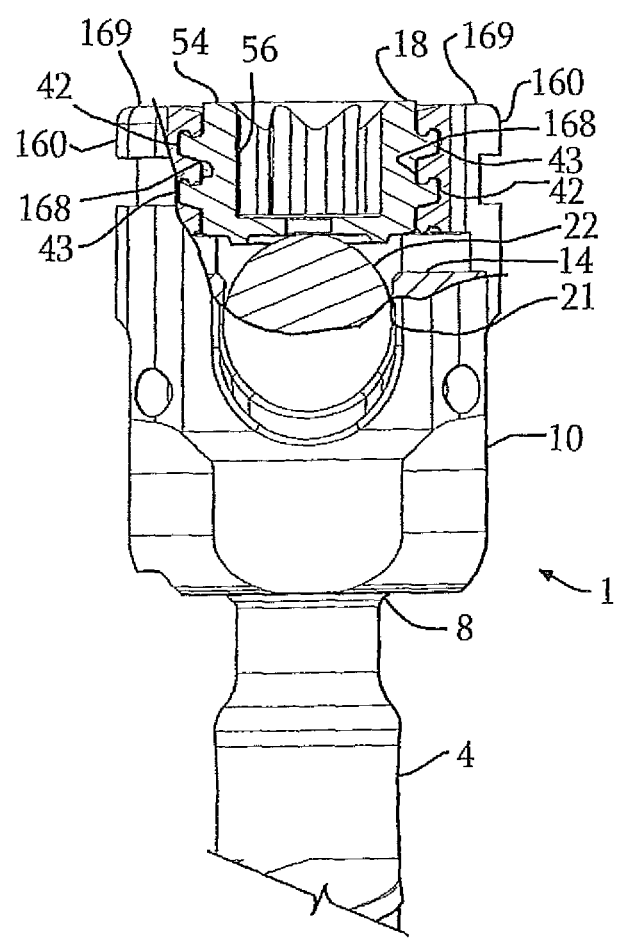
FIG. 8 a partial front elevational view of an open bone screw assembly, with portions broken away to show the detail thereof, including a receiver, a shank, a compression insert and also shown in engagement with the closure top of FIG. 1 (in reduced view) and a longitudinal connecting member in the form of a hard rod.

With reference to FIGS. 1-8, and in particular to FIG. 8, the reference number 1 generally represents an open implant in the form of a polyaxial bone screw apparatus or assembly that cooperates with an illustrated closure structure 18 embodiment of the invention. The bone screw assembly 1 is described in detail in U.S. Provisional Patent Application No. 61/631,746 filed Jan. 10, 2012 and incorporated by reference herein (hereafter the '746 application) and therefore will not be described in great detail herein. The description set forth in the '746 application includes a more detailed explanation of all the components referenced in FIG. 8. It is noted that multi-start closure embodiments of the invention, such as the closure 18 may be used with a variety of open implants including, but not limited to a wide variety of polyaxial screws, mono-axial or fixed screws, hooks and other types of open implants requiring a plug or closure mechanism to fix a rod or other implant member to a vertebra or other bone. Thus, the assembly 1 is only one example of how multi-start closures of the invention may be used.

Briefly, the illustrated assembly 1 includes a shank 4 with an upwardly extending upper portion or capture structure 8; an open receiver 10; a retaining structure or retainer (not shown) that pivots with the shank 4, a compression or pressure insert 14 and the multi-start closure structure or plug 18 in the form of a cylindrical plug having a double-start helically wound flange-form. The closure structure 18 presses against and captures a longitudinal connecting member, for example, a rod 21 which in turn engages the compression insert 14 that presses against the shank upper portion 8 that is attached to the retaining structure that in turn presses against an inner surface of the receiver 10, so as to capture and fix the longitudinal connecting member 21 within the receiver 10 and thus fix the member 21 relative to a vertebra (not shown). The illustrated receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The illustrated rod 21 is hard, stiff, non-elastic and cylindrical, having an outer cylindrical surface 22. However, in other embodiments, the rod 21 may be elastic, deformable and/or of a different cross-sectional geometry. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes. Furthermore, in lieu of a rod, longitudinal connecting members for use with the assembly 1 may take a variety of shapes, and/or may include a tensioned cord as described in greater detail in the '746 application that is incorporated by reference herein.

It is noted that the receiver 10 includes guide and advancement structures 168 that are shown as interlocking flange forms described in greater detail in applicant's U.S. Pat. No. 6,726,689, also incorporated by reference herein. Alternately, when the closure structure includes a different helical form, the receiver cooperating structures (e.g., 168) must also be of a cooperating, mating geometry, such as a square-shaped thread receiving form, a buttress thread receiving form, a reverse angle thread receiving form or other thread-like or non-thread-like helically wound discontinuous advancement structure receiving forms for operably guiding under rotation and advancing a multi-start closure structure downward between the receiver arms 160, as well as eventual torquing when the closure structure abuts against the rod 21 or other connecting member.

With particular reference to FIGS. 1-7, the illustrated multi-start closure structure 18 is a double start closure having a substantially cylindrical plug body 40 having an axis of rotation that is the same as that of the receiver 10 and including a helically wound guide and advancement structure in the form of a pair of helically wound forms 42 and 43, each illustrated as an interlocking flange form that operably joins with mating flange form guide and advancement structures 168 disposed on the arms of the receiver 10. The form 42 includes a start surface or structure 46 and the form 43 includes a start surface or structure 47. Each helically wound form 42 and 43 may take a variety of forms and geometries, including those described in Applicant's U.S. Pat. No. 6,726,689, which is incorporated by reference herein. It is noted (and also described in greater detail subsequently herein) that each of the closure structure guide and advancement structures or forms 42 and 43 could alternatively be in the form of a buttress thread, a square thread, a reverse angle thread, a v-thread or other thread like or non-thread like helically wound advancement structures, for operably guiding under rotation and advancing the closure structure downward between the arms of the receive 10 and preferably having such a nature as to resist splaying of the receiver arms when the closure structure 18 is advanced into the receiver channel. The specific flange forms 42 and 43 illustrated in FIGS. 1-7, as well as acceptable alternative locking forms, are described in detail in Applicant's U.S. Pat. No. 6,726,689, incorporated by reference herein, and thus shall not be discussed further herein. Such interlocking flange forms are preferred as the added strength provided thereby beneficially cooperate with and counter any reduction in strength caused by the any reduced profile of the receiver 10 that may more advantageously engage longitudinal connecting member components.

The illustrated closure structure 18 also includes a top surface 54 with an internal drive 56 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 56 is used for both rotatable engagement and, if needed, disengagement of the closure 18 from the receiver 10 at arms 160. A base or bottom surface 58 of the closure is planar and further includes a rim 60 for engagement and penetration into the surface 22 of the rod 21 in certain embodiments of the invention. The closure top 18 further includes a cannulation through bore 62 extending along a central axis thereof and through a drive base surface 63 and the bottom surface 58 thereof. Such a through bore provides a passage through the closure 18 interior for a length of wire (not shown) inserted therein to provide a guide for insertion of the closure top into the receiver arms 160.

Figure 1:
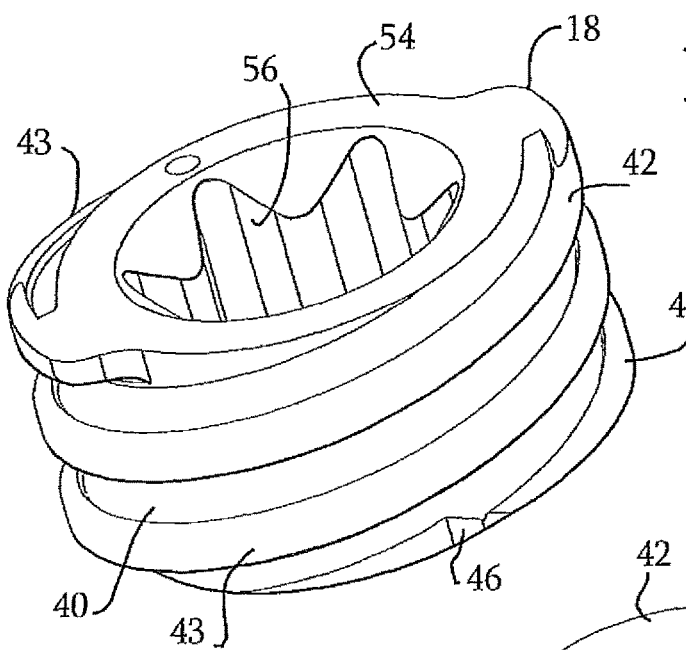
FIG. 1 is a perspective view of an embodiment of a multi-start closure according to the invention.
Figure 2:
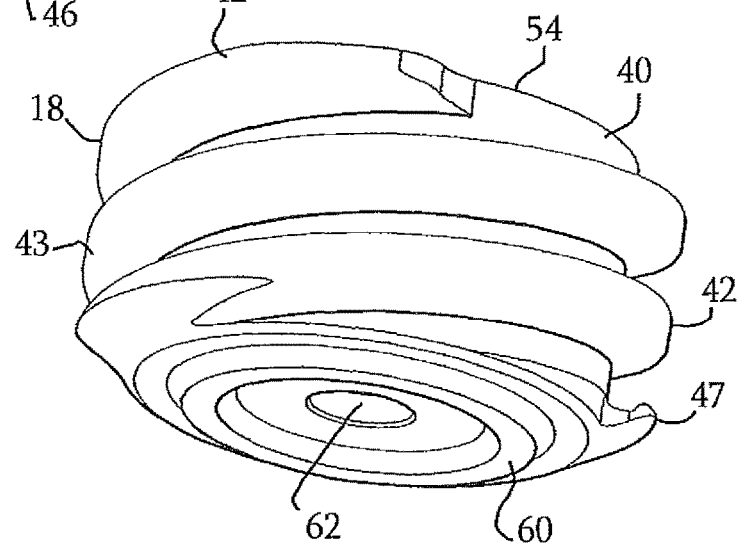
FIG. 2 is another perspective view of the multi-start closure of FIG. 1.
Figure 3:
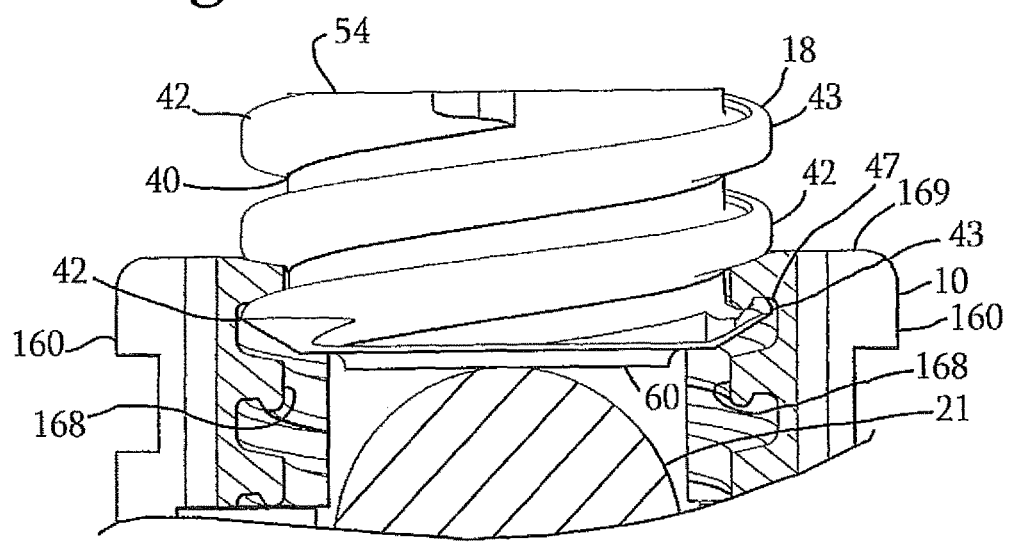
FIG. 3 is a front elevational view of the closure of FIG. 1 shown with a portion of a receiver of a polyaxial bone screw according to FIG. 8, the receiver shown in partial front elevation with portions broken away to show the detail thereof, and further showing a rod being pressed upon by the closure, the rod also in partial front elevation with portions broken away to show the detail thereof.
Figure 4:
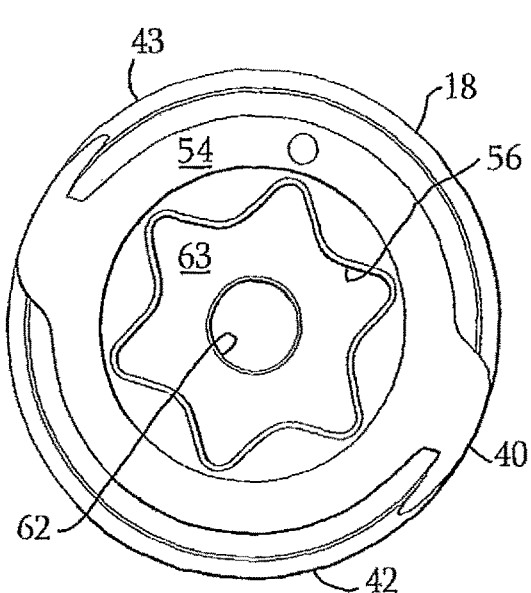
FIG. 4 is a reduced top plan view of the closure of FIG. 1.
Figure 5:
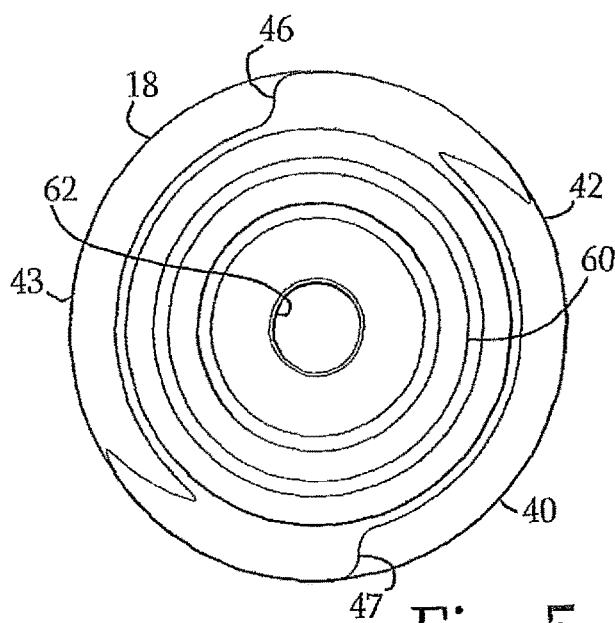
FIG. 5 is a reduced bottom plan view of the closure of FIG. 1.
Figure 6:
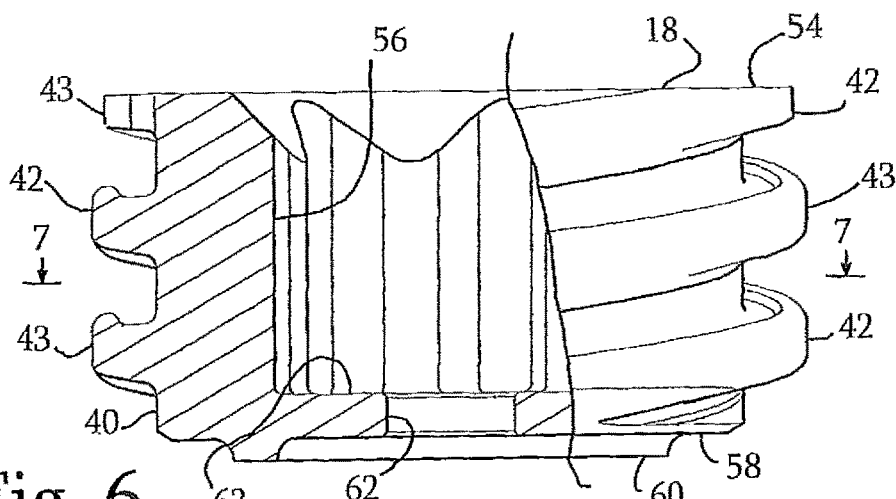
FIG. 6 is an enlarged front elevational view of the closure of FIG. 1 with portions broken away to show the detail thereof.
Figure 7:
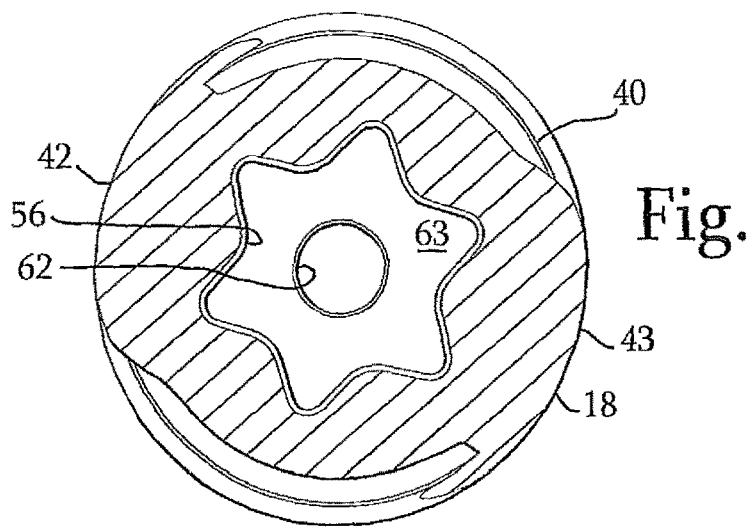
FIG. 7 is a reduced cross-sectional view taken along the line 7-7 of FIG. 6.

The closure structure 18 helically wound flange form start structures 46 and 47 of the respective forms 42 and 43 are located on opposite sides of the closure plug body 40 and are both located adjacent the bottom surface 58. As illustrated in FIG. 3, for example, when the closure structure 18 is rotated into the receiver 10 between receiver arms 160, each having a guide and advancement structure 168, the start 46 engages mating guide and advancement structure 168 on one arm 160 and the start 47 simultaneously engages guide and advancement structure 168 on the opposing arm 160, both forms 42 and 43 being simultaneously captured by the mating forms 168 on the opposed arms 160. As the structure 18 is rotated, the structure advances axially downwardly between the arms 160 and presses evenly down upon the captured rod 21. Each time the illustrated duel- or double-start closure plug 18 is rotated one complete turn or pass (three hundred sixty degrees) between the implant arms, the closure plug 18 advances axially into the implant and toward the rod by a width of two helical flange forms. The illustrated closure 18 is sized for at least one complete rotation (three hundred sixty degree) of the plug 18 with respect to the receiver 10 open arms 160 to substantially receive the plug between the implant arms. Each of the start structures 46 and 47 includes a leading face having at least one curvate surface. The at least one curvate surface includes at least one radius of curvature. In one embodiment, the at least one curvate surface is both concave and convex. Multi-start closures of the invention may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms of the multi-start closure of the invention are sized so as to spiral around a cylindrical plug body thereof to an extent that the closure rotates at least ninety-one degrees to fully or substantially receive the closure plug between the arms of the bone screw receiver or other open implant. Particularly preferred guide and advancement structures are sized for at least one complete turn or pass (three-hundred sixty degree) of the closure between the receiver 10 arms and as many as two to three rotations to be fully received between implant arms.

In use, the receiver 10, the retainer 12 and the compression insert 14 are assembled with the shank 4 either before or after the shank is implanted into a vertebra, and the resulting assembly 1 is ultimately attached to the rod 21 or other longitudinal connecting member as described in the '746 application incorporated by reference herein. It is noted that the shank 4 and other bone screw assembly parts, the rod 21 (also having a central lumen in some embodiments) and the closure top 18 having the central bore 62 can be inserted in a percutaneous or minimally invasive surgical manner, utilizing guide wires. After the rod 21 or other longitudinal connecting member is positioned in an open or percutaneous manner in cooperation with the at least two bone screw assemblies 1 (or other open implants), the closure structure 18 is then inserted into and advanced between the arms 160 of each of the receiver 10. The closure structure 18 is rotated, using a tool engaged with the inner drive 56 until a selected pressure is reached at which point the rod 21 engages a U-shaped seating surface of the compression insert 14, further pressing the insert against the shank upper portion 8 and attached retainer into locked frictional engagement with the receiver 10. Prior to locking the insert 14 against the shank head 8, the shank 4 may be pivoted to a plurality of potentially desirable positions with respect to the receiver 10, followed by locking of the polyaxial mechanism by fully mating the multi-start closure top 18 with the receiver 10. Different angular or articulated positions of the shank 4 with respect to the receiver 10 are shown in the '746 application incorporated by reference herein.

With specific reference to FIGS. 3 and 8, as the multi-start closure structure 18 rotates and moves downwardly into the respective receiver 10, the rim 60 engages and penetrates the rod surface 22, the closure structure 18 pressing downwardly against and biasing the rod 21 into compressive engagement with the insert 14 that urges the shank upper portion 8 and attached retainer into locking engagement with the receiver, the retainer outer surface frictionally abutting an inner spherical seating surface of the receiver 10. For example, about 80 to about 120 inch pounds of torque on the closure top may be applied for fixing the bone screw shank 6 with respect to the receiver 10. Also, for example, when the shank 4 is disposed at an angle with respect to the receiver 10, a part of the shank upper portion 8 may also be in frictional engagement with a portion of the receiver spherical seating surface.

If removal of the rod 21 from any of the bone screw assemblies 1 is necessary, or if it is desired to release the rod 21 at a particular location, disassembly is accomplished by using the driving tool (not shown) that mates with the internal drive 56 on the closure structure 18 to rotate and remove such closure structure from the cooperating receiver 10. Disassembly is then accomplished in reverse order to the procedure described previously herein for assembly.

Figure 9:
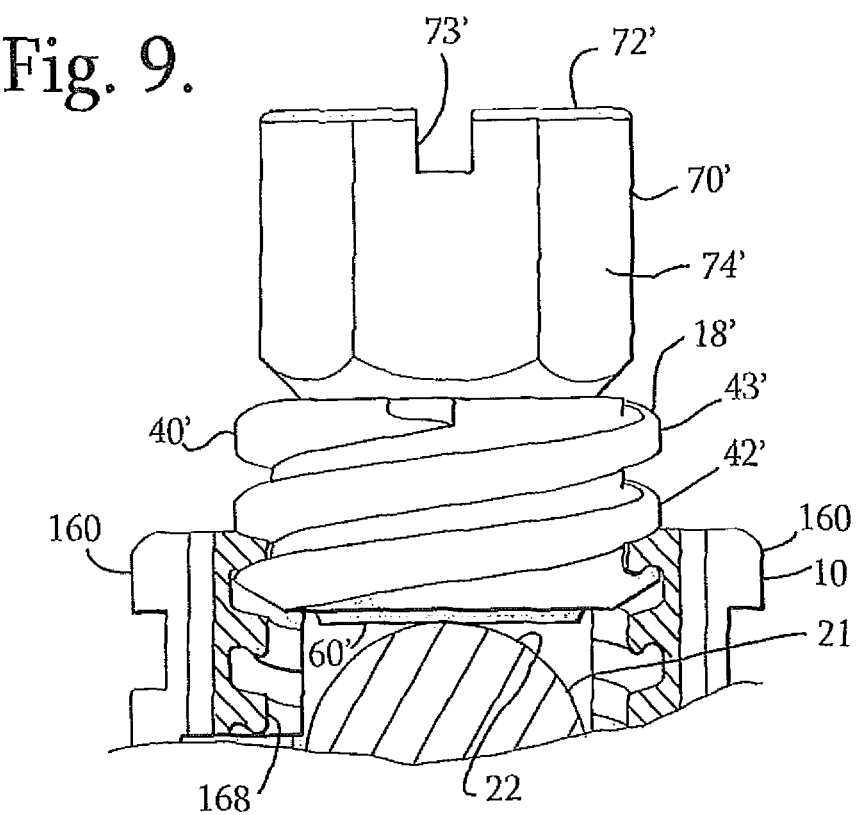
FIG. 9 is a front elevational view of an alternative closure of an embodiment of the invention, similar to the closure of FIG. 1, but including a break-off head, the alternative closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.
Figure 10:
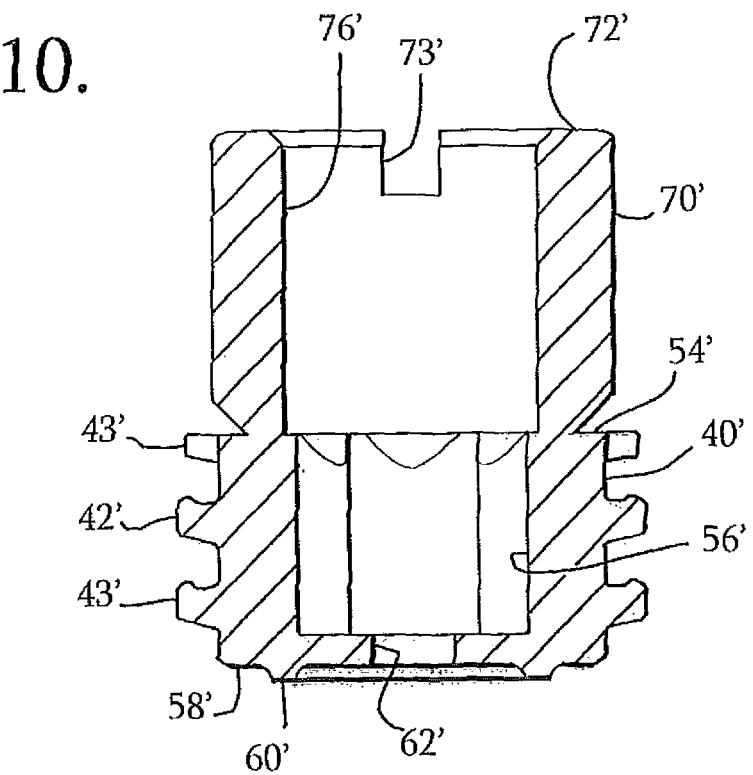
FIG. 10 is another front elevational view of the closure of FIG. 9 with portions broken away to show the detail thereof.

With reference to FIGS. 9 and 10, an alternative closure top 18' is shown that is almost identical to the closure top 18. However, the top 18' differs from the top 18 in that the top 18' includes a break-off head 70' that further includes a top surface 72' having tooling notches 73', an outer faceted driving surface 74', illustrated as having a hex-shaped profile, and an inner bore 76'. Otherwise, the closure top 18' includes a body 40', a first helical form 42', a second helical form 43', a body top surface 54', a body internal drive 56', a base 58', a rim 60', a cannulation bore 62' and a drive base surface 63' that is the same or substantially similar to the respective body 40, first helical form 42, second helical form 43, body top surface 54, internal drive 56, base 58, rim 60, cannulation bore 62 and drive base surface 63 previously described herein with respect to the closure top 18. The break-off head 70' is integral with the body 40' at the body top surface 54'. The inner bore 76' communicates with the inner drive 56' and the cannulation bore 62'. The break-off head 70' is designed to allow such head 70' to break from the body 40' at or near the top surface 54' at a preselected torque, for example, 70 to 140 inch pounds, when a hex-shaped tool (not shown) engages the outer surfaces 74' and drives the closure structure 18' into the receiver 10 as shown in FIG. 9. The inner drive 56' is used for disassembly or loosening of the closure 18' from the receiver 10, and re-tightening, if needed.

Figure 11:
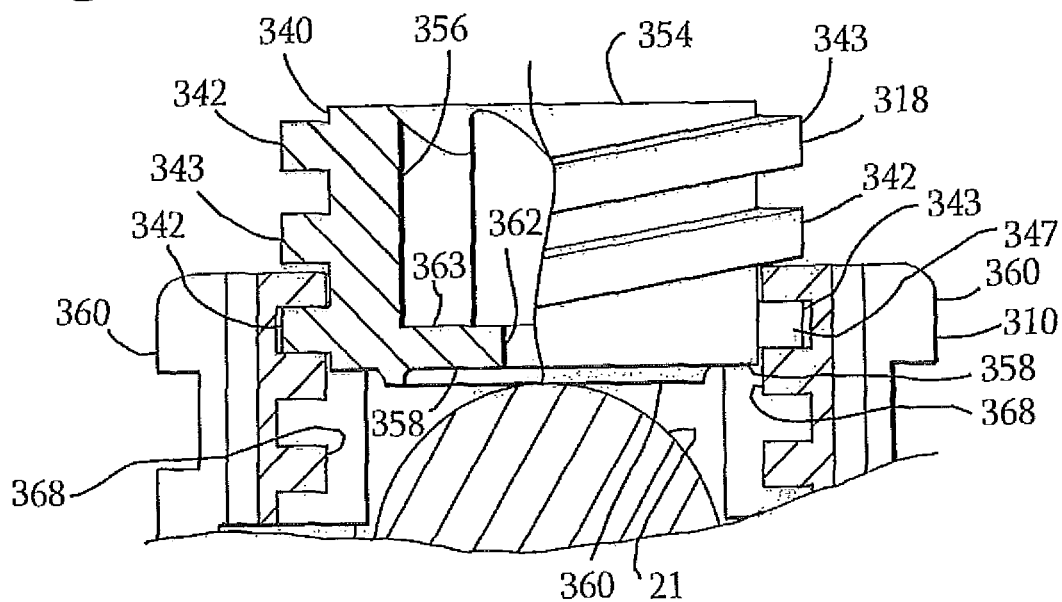
FIG. 11 is a front elevational view of an alternative square-thread closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 11, another alternative multi-start closure top 318 is shown that is almost identical to the closure top 18 with the exception that the two flange forms 42 and 43 with respective starts 46 and 47 have been replaced with square threads 342 and 343 with respective starts 346 (not shown) and 347. Otherwise, the dual or double start closure top 318 includes a body 340, a body top surface 354, a body internal drive 356, a base 358, a rim 360', a cannulation bore 362 and a drive base surface 363 that is the same or substantially similar to the respective body 40, body top surface 54, internal drive 56, base 58, rim 60, cannulation bore 62 and drive base surface 63 previously described herein with respect to the closure top 18. In FIG. 11, the closure top 318 is shown partially wound into a polyaxial bone screw receiver 310 having opposed arms 360 with inner surfaces equipped with guide and advancement structures 368 that are sized and shaped to simultaneously closely receive and mate with the square threads 342 and 343 of the double closure structure 318. Otherwise, the receiver 310 is identical or substantially similar to the receiver 10 described in detail in the '746 application incorporated by reference herein.

Figure 12:
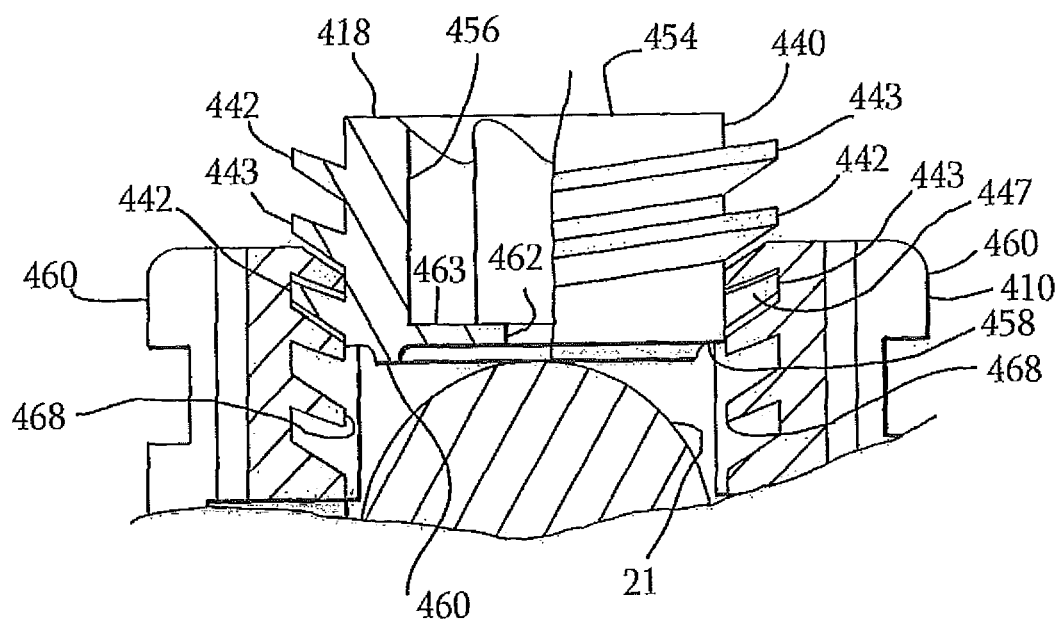
FIG. 12 is a front elevational view of an alternative reverse angle closure of an embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 12, an alternative multi-start closure top 418 is shown that is almost identical to the closure top 18 with the exception that the two flange forms 42 and 43 with respective starts 46 and 47 have been replaced with reverse angle threads 442 and 443 with respective starts 446 (not shown) and 447. Otherwise, the dual or double start closure top 418 includes a body 440, a body top surface 454, a body internal drive 456, a base 458, a rim 460', a cannulation bore 462 and a drive base surface 463 that is the same or substantially similar to the respective body 40, body top surface 54, internal drive 56, base 58, rim 60, cannulation bore 62 and drive base surface 63 previously described herein with respect to the closure top 18. The closure top 418 is shown partially wound into a polyaxial bone screw receiver 410 having opposed arms 460 with inner surfaces equipped with guide and advancement structures 468 that are sized and shaped to simultaneously closely receive and mate with the reverse angle threads 442 and 443 of the double start closure structure 418. Otherwise, the receiver 410 is identical or substantially similar to the receiver 10 described in detail in the '746 application incorporated by reference herein.

Figure 13:
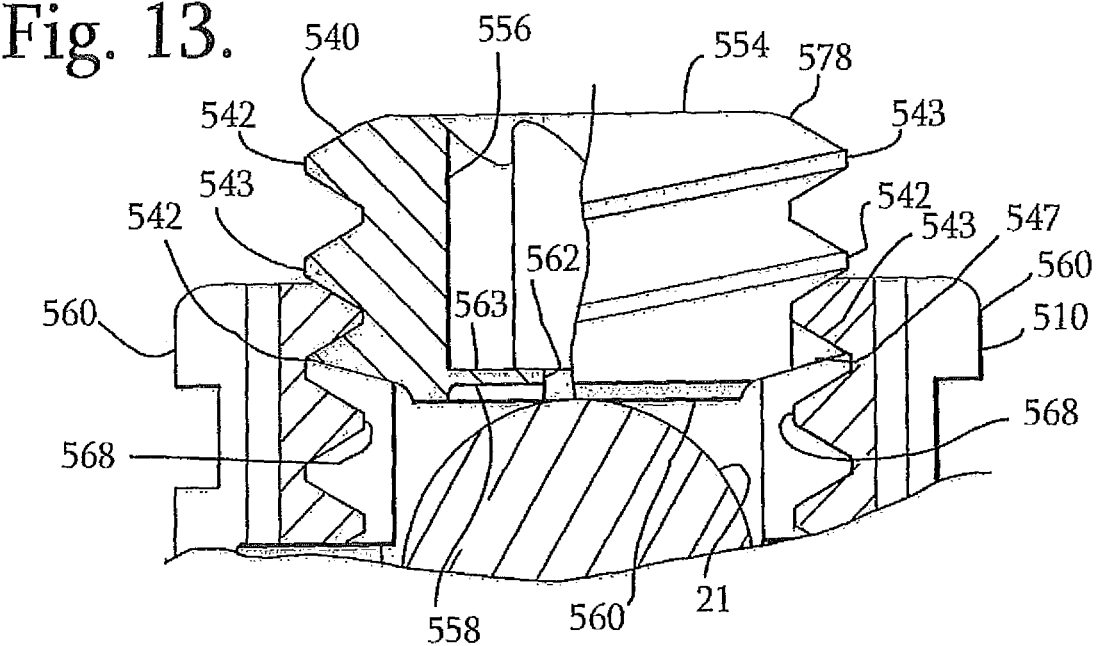
FIG. 13 is a front elevational view of an alternative v-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 13, another alternative multi-start closure top 518 is shown that is almost identical to the closure top 18 with the exception that the two flange forms 42 and 43 with respective starts 46 and 47 have been replaced with v-threads 542 and 543 with respective starts 546 (not shown) and 547. Otherwise, the dual or double start closure top 518 includes a body 540, a body top surface 554, a body internal drive 556, a base 558, a rim 560', a cannulation bore 562 and a drive base surface 563 that is the same or substantially similar to the respective body 40, body top surface 54, internal drive 56, base 58, rim 60, cannulation bore 62 and drive base surface 63 previously described herein with respect to the closure top 18. The closure top 518 is shown partially wound into a polyaxial bone screw receiver 510 having opposed arms 560 with inner surfaces equipped with guide and advancement structures 568 that are sized and shaped to simultaneously closely receive and mate with the threads 542 and 543 of the double start closure structure 518. Otherwise, the receiver 510 is identical or substantially similar to the receiver 10 described in detail in the '746 application incorporated by reference herein.

Figure 14:
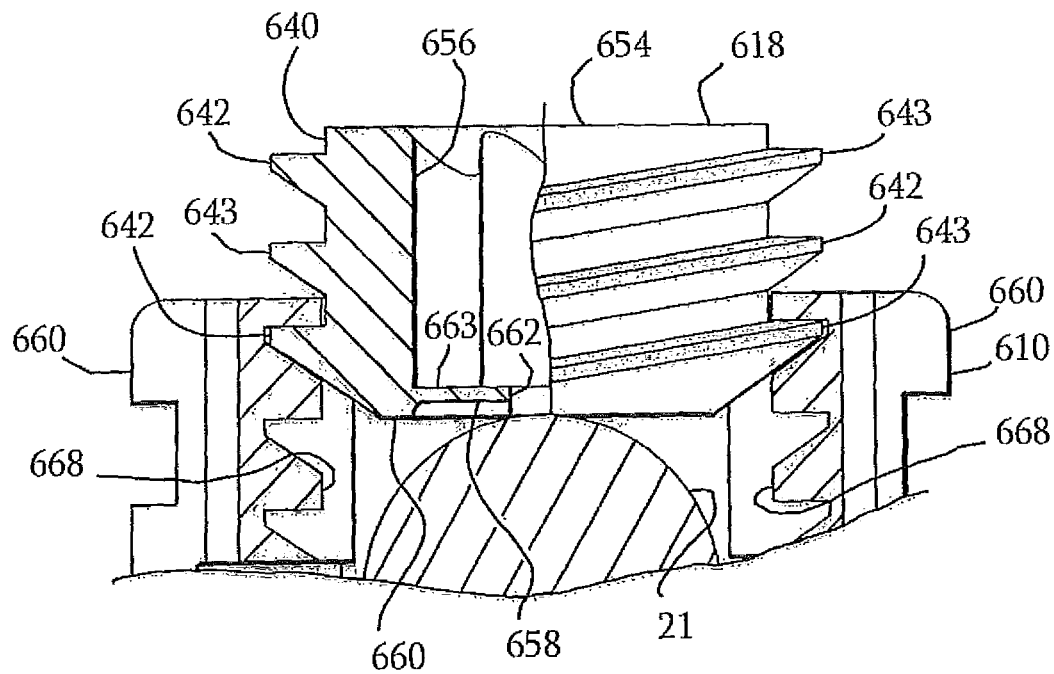
FIG. 14 is a front elevational view of an alternative buttress-thread closure embodiment of the invention with portions broken away to show the detail thereof, the closure shown with a portion of a receiver of the polyaxial bone screw of FIG. 8 shown in enlarged and partial front elevation with portions broken away to show the detail thereof, and further showing a rod being pressed upon by the alternative closure, the rod also in partial front elevation with portions broken away to show the detail thereof.

With reference to FIG. 14, another alternative multi-start closure top 618 is shown that is almost identical to the closure top 18 with the exception that the two flange forms 42 and 43 with respective starts 46 and 47 have been replaced with buttress threads 642 and 643 with respective starts 446 and 447 (not shown). Otherwise, the dual or double start closure top 618 includes a body 640, a body top surface 654, a body internal drive 656, a base 658, a rim 660', a cannulation bore 662 and a drive base surface 663 that is the same or substantially similar to the respective body 40, body top surface 54, internal drive 56, base 58, rim 60, cannulation bore 62 and drive base surface 63 previously described herein with respect to the closure top 18. The closure top 618 is shown partially wound into a polyaxial bone screw receiver 610 having opposed arms 660 with inner surfaces equipped with guide and advancement structures 668 that are sized and shaped to simultaneously closely receive and mate with the buttress threads 642 and 643 of the double start closure structure 618. Otherwise, the receiver 610 is identical or substantially similar to the receiver 10 described in detail in the '746 application incorporated by reference herein.

With reference to FIGS. 15 and 16, an open receiver 710 is illustrated that is substantially similar to the receiver 10 previously described herein with the exception that the receiver 710 includes opposed arms 760, each having an integral upstanding break-off extension 761. Each receiver arm 760 and integral extension 761 has an inner helically wound guide and advancement structure 768 that is sized and shaped to mate with the flange forms 42 and 43 of the dual start closure 18 previously described herein. The break-off extensions 761 are initially integral with the respective arms 760 and are then broken off by a user after the closure 18 has been rotatingly advanced along the arm extensions 761 and into the channel located between the receiver arms 760. In the illustrated embodiment, in addition to an outer groove or notch 770 located at or near a top surface 769 of each of the arms 760 where the extensions 761 break off from the receiver arms, illustrated inner arm surfaces include a recess or cut 771, best shown in FIG. 16, that runs substantially horizontally. Each recess 771 is curved and elongate and disposed somewhat cross-wise or transverse to the respective flange form 768. For example, with reference to the arm 760 shown in FIG. 16, the recess 771 cuts into a weakened region, generally 780, where the arm 760 joins with the respective attached adjacent extension 761, the curved and elongate recess 771 beginning at a lower portion or location 781 of the flange form recess or segment and terminating at an opposed upper end location of the flange form segment, while otherwise leaving the flange form 768 intact. Stated in another way, the substantially horizontally extending recess 771 cuts into both a lead portion and a trailing portion of each of the flange form segments located near and directly above the opposed arms 760 and substantially opposite the notch 770, thus further weakening the region where the extension and the arm attach, without destroying the flange form path, so that the closure 18 is not derailed by the recess 771 or otherwise prohibited from moving downwardly into the receiver channel formed between the receiver arms 760.

With reference to FIG. 17, the multi-start closure 18 is shown cooperating with a spinal implant receiver, such as a bone screw receiver 10' and a discrete, detachable guide tool 801. The elongate guide tool 801, only partially shown in FIG. 17, is typically sized for extending from the bone screw receiver 10' upwardly to a location outside of a patient, the tool providing a guide channel for operably guiding the rod 21 or other longitudinal connecting member from a position exterior of the bone screw receiver 10' toward and into the bone screw receiver 10'. The illustrated guide tool has opposed arms 805, each arm having a helical guide and advancement structure 810 thereon that is illustrated as a square thread form, but may be of other geometry, including a flange form the same or similar to the flange forms 168' of the receiver 10' that mates with the flange forms 42 and 43 of the closure structure 18. Thus, the illustrated structures 810 are sized and shaped for receiving and rotating engagement with a dual start closure. The closure 18 is shown partially wound into the receiver 10' that is identical or substantially similar to the receiver 10 with the exception of certain outer arm surface features (not shown). Thus, the receiver 10' includes opposed arms 160' with inner surfaces having guide and advancement structures 168' that are sized and shaped to simultaneously closely receive and mate with the flange forms 42 and 43 of the dual start closure structure 18. The guide tool 801 includes attachment structure for detachable attachment to the receiver 10' (not shown), that may take a variety of forms and methods, including, but not limited to a slide-on, slide-off attachment, a snap-on, rotate off attachment, a rotate-on and rotate-off attachment, to name a few. For example, cooperating attachment structure for both the tool and the receiver may be used that is disclosed in U.S. Pat. No. 7,470,279 and incorporated by reference herein. Returning to the inner helically wound guide and advancement structure 810 formed on each arm 804 of the guide tool 801, the structure 810 is sized and shaped for being aligned with the receiver arms 160' during removable attachment of the tool 801 with the respective bone screw receiver 10' so as to continue the helical pathway for the closure 18, the structures 810 being synchronized with the flange forms 168' to allow for the rotation and driving transfer of the closure 18 from the tool 801 into the receiver 10'.

It is to be understood that while certain forms of the present invention have been illustrated and described herein, it is not to be limited to the specific forms or arrangement of parts described and shown.

The invention claimed is:

1. A medical implant assembly comprising:
    a receiver having a first arm and a second arm spaced apart from each other by a channel, the first arm and the second arm each having a top surface and an inner surface having a first thread on the first arm and a second thread on the second arm comprising discontinuously helically wound threads being symmetrically and diametrically opposed to each other and extending up to the top surface on each arm, the opposed discontinuously helically wound threads forming a dual lead in closure starting arrangement for the receiver;
    a closure having a longitudinal axis with an outer surface having a first continuously helically wound thread form and a second continuously helically wound thread form, the first continuously helically wound thread form having a first start structure with a leading face surface extending below a first upper loading surface disposed between a root and a crest of the first continuously helically wound thread form, the second continuously helically wound thread form having a second start structure with a leading face surface extending below a second upper loading surface disposed between a root and a crest of the second continuously helically wound thread form, the leading face surface on each of the first start structure and the second start structure including at least one curvate surface;
    the channel positioned between the first arm and the second arm and opening onto the top surface, the channel adapted to receive a longitudinal connecting member, the channel closeable with the closure having an axis of rotation;
    the first discontinuously helically wound thread form on the inner surface of the first arm having a first lower loading surface, the first start structure being rotatably advanceable under the first discontinuously helically wound thread form and the first lower loading surface being mateable with the first upper loading surface; and
    the second discontinuously helically wound thread form on the inner surface of the second arm having a second lower loading surface, the second start structure being rotatably advanceable under the second discontinuously helically wound thread form and the second lower loading surface being mateable with the second upper loading surface, a rotation of the closure about the axis of rotation between the first arm and the second arm causing a simultaneous advancement of the first start structure under the first discontinuously helically wound thread form and the second start structure under the second discontinuously helically wound thread form and a mating of the first and second lower loading surface with the first and second upper loading surface, respectively, the closure rotationally advanceable within the channel until the closure locks the longitudinal connecting member within the channel.

2. The medical implant assembly of claim 1, further comprising:
    a guide tool having a first guide arm and a second guide arm detachably attached to the receiver;
    a third discontinuously helically wound thread form on the first guide arm; and
    a fourth discontinuously helically wound thread form on the second guide arm, the first start structure threadably engageable with the third discontinuously helically wound thread form simultaneously with the second start structure threadably engageable with the fourth discontinuously helically wound thread form when the closure is rotated between the first guide arm and the second guide arm, the third discontinuously helically wound thread form and the fourth discontinuously helically wound thread form adapted to transfer the closure between the guide tool and the receiver.

3. The medical implant assembly of claim 1, wherein the first continuously helically wound thread form and the second continuously helically wound thread form are each flange forms.

4. The medical implant assembly of claim 1, wherein the first continuously helically wound thread form and the second continuously helically wound thread form are each one of: v-threads, square threads, reverse angle threads, or buttress threads.

5. The medical implant assembly of claim 1, wherein the first start structure is disposed at a diametrically opposite location on the closure from the second start structure.

6. The medical implant assembly of claim 1, wherein each of the continuously first and the second helically wound thread form is disposed at a top of the closure, the first helically wound thread form and the second helically wound thread form each extending along the outer surface of the closure to a bottom of the closure and ending at the first and the second start structure, respectively.

7. The medical implant assembly of claim 1, wherein the at least one curvate surface of both the first start structure and the second start structure is defined by at least one radius of curvature, the at least one radius of curvature being less than a radius of curvature for an outer surface on the crest of the first continuously helically wound thread form.

8. The medical implant assembly of claim 1, wherein the at least one curvate surface of both the first start structure and the second start structure is defined by at least one radius of curvature, the at least one radius of curvature being less than a radius of curvature for an outer surface on the crest of the second continuously helically wound thread form.

9. The medical implant assembly of claim 1, wherein the at least one curvate surface includes both a convex surface and concave surface.

10. The medical implant assembly claim of 9, wherein both of the concave surface and the convex surface of the first start structure are positioned between the root and the crest of the first continuously helically wound thread form, and wherein both of the concave surface and the convex surface of the second start structure are positioned between the root and the crest of the second continuously helically wound thread form.

11. The medical implant assembly of claim 10, wherein the concave surface is adjacent the root and the convex surface is adjacent the crest of the first and second start structures for the first and second continuously helically wound thread form, respectively.

12. The medical implant assembly of claim 9, wherein a radius of curvature of the convex surface is substantially equal to a radius of curvature of the concave surface.

13. The medical implant assembly of claim 9, wherein each of the first start structure and the second start structure includes a bottom beveled surface.

14. The medical implant assembly of claim 1, wherein the first and second start structure leading face surfaces are at least partially planar surfaces parallel with respect to each other.

15. The medical implant assembly of claim 1, wherein each of the at least one curvate surfaces is substantially parallel to the closure longitudinal axis.

16. The medical implant assembly of claim 1, wherein each of the at least one curvate surface includes both a convex surface and concave surface.

17. The medical implant assembly of claim 1, wherein each of the at least one curvate surfaces is a concave surface.

18. The medical implant assembly of claim 1, wherein the closure first continuously helically wound thread form includes a first lower surface disposed between the root and the crest and the closure second continuously helically wound thread form includes a second lower surface disposed between the root and the crest, and wherein the leading face surface of the first start structure extends between the first upper surface and the first lower surface and the leading face surface of the second start structure extends between the second upper surface and the second lower surface.

19. The medical implant assembly of claim 18, wherein each of the leading face surfaces of the first start structure and the second start structure include at least a partial planar surface.

20. The medical implant assembly of claim 1, wherein the receiver first arm and the second arm top surface each include a breakoff extension with an inner surface having a discontinuously helically wound thread form, the first arm breakoff extension thread form being continuous with the first discontinuously helically wound thread form on the inner surface of the first arm and the second arm breakoff extension thread form being continuous with the second discontinuously helically wound thread form on the inner surface of the second arm.

21. A medical implant assembly comprising:
a receiver having a first arm and a second arm spaced apart from each other by a rod-receiving channel, the first arm and the second arm each having a top surface and an inner surface having a first thread on the first arm and a second thread on the second arm comprising first and second discontinuously helically wound threads, respectively, being symmetrically and diametrically opposed to each other and extending up to the top surface on each arm, the opposed discontinuously helically wound threads forming a dual lead in closure starting arrangement for the receiver;
a closure having a first continuously helically wound thread form and a second continuously helically wound thread form, the first continuously helically wound thread form having a first start structure and a first loading surface extending between a root and a crest of the first continuously helically wound thread form, the second continuously helically wound thread form having a second start structure and a second loading surface extending between a root and a crest of the second continuously helically wound thread form, each of the first start structure and the second start structure having a leading face surface extending below each closure loading surface and including at least a partial concave surface;
the channel being formed by the first arm and the second arm, the channel closeable with the closure having an axis of rotation;
the first discontinuously helically wound thread form on the inner surface of the first arm having a first discontinuous loading surface, the first start structure rotatable under the first discontinuously helically wound thread form and the first discontinuous loading surface mateable with the closure first loading surface; and
the second discontinuously helically wound thread form on the inner surface of the second arm having a second discontinuous loading surface, the second start structure rotatable under the second discontinuously helically wound thread form and the second discontinuous loading surface mateable with the closure second loading surface, a rotation of the closure about the axis of rotation between the first arm and the second arm causing the first start and the second start structures to simultaneously rotatably advance under the first discontinuously helically wound thread form and the second discontinuously helically wound thread form, respectively, the closure rotationally advanceable within the channel until a rod positioned within the channel is locked therein.

22. The medical implant assembly of claim 21, wherein the closure has a bottom surface that is closed.

23. The medical implant assembly of claim 22, wherein the bottom surface is flat.

24. The medical implant assembly of claim 21, wherein the first continuously helically wound thread form and the second continuously helically wound thread form are each one of: v-threads, square threads, reverse angle threads, or buttress threads.

25. The medical implant assembly of claim 21, wherein the first continuously helically wound thread form and the second continuously helically wound thread form are each flange forms.

26. A medical implant assembly comprising:
a receiver having a first arm and a second arm spaced apart from each other by a rod-receiving channel, the first arm and the second arm each having a top surface and an inner surface having a first thread on the first arm and a second thread on the second arm comprising first and second discontinuously helically wound threads, respectively, being symmetrically and diametrically opposed to each other and extending up to the top surface on each arm, the opposed discontinuously helically wound threads forming a dual lead in closure starting arrangement for the receiver;
a closure having a first continuously helically wound thread form and a second continuously helically wound thread form, each of the first continuously helically wound thread form and the second continuously helically wound thread form being a reverse angle thread, the first continuously helically wound thread form having a first start structure and a first upper loading surface extending between a root and a crest of the first continuously helically wound thread form, the second continuously helically wound thread form having a second start structure and a second upper loading surface extending between a root and a crest of the second continuously helically wound thread form, each of the first start structure and the second start structure having a leading face extending below their respective upper loading surfaces, each leading face including at least a partial concave surface and a partial convex surface;
the channel being formed by the first arm and the second arm opening onto the top surface, the channel adapted to receive a rod, the channel closeable with the closure having an axis of rotation;
the first discontinuously helically wound thread form on the inner surface of the first arm being a reverse angle thread having a first lower loading surface, the first start structure rotatable under the first discontinuously helically wound thread form and the first lower loading surface threadably engageable to the first upper loading surface; and
the second discontinuously helically wound thread form on the inner surface of the second arm being a reverse angle thread having a second lower loading surface, the second start structure rotatable under the second discontinuously helically wound thread form and the second lower loading surface threadably engageable to the second upper loading surface, a rotation of the closure about the axis of rotation between the first arm and the second arm causing a simultaneous mating of the first continuously helically wound thread form with the first discontinuously helically wound thread form and the second continuously helically wound thread form with the second discontinuously helically wound thread form, the closure rotationally advanceable within the channel until the closure locks the rod received within the channel.

27. The medical implant assembly of claim 26, wherein the concave surface is adjacent the root and the convex surface is adjacent the crest for each of the first and second continuously helically wound thread forms.

28. The medical implant assembly of claim 26, wherein the first start structure is disposed at a diametrically opposite location on the closure from the second start structure.

\* \* \* \* \*